United States Patent [19]

Weiss et al.

[11] Patent Number: 5,453,200
[45] Date of Patent: Sep. 26, 1995

[54] PRECIPITATION PROCESS FOR EXOCELLULAR PROTEINS

[75] Inventors: Albrecht Weiss, Langenfeld; Wolfgang Berke, Kuerten-Duerscheid, both of Germany

[73] Assignee: Henkel Kommanditgesellschaft auf Aktien, Duesseldorf, Germany

[21] Appl. No.: 66,102

[22] PCT Filed: Nov. 18, 1991

[86] PCT No.: PCT/EP91/02170

§ 371 Date: May 26, 1993

§ 102(e) Date: May 26, 1993

[87] PCT Pub. No.: WO92/09687

PCT Pub. Date: Jun. 11, 1992

[30] Foreign Application Priority Data

Nov. 26, 1990 [DE] Germany ............... 40 37 530.7

[51] Int. Cl.$^6$ ................................................ B01D 15/00
[52] U.S. Cl. .................... 210/639; 210/650; 210/665; 210/666; 210/669; 210/694; 435/183; 435/815
[58] Field of Search ................... 210/638, 639, 210/650, 663, 665, 667, 691, 666, 669, 694; 435/183, 815

[56] References Cited

U.S. PATENT DOCUMENTS

| 3,101,302 | 8/1963 | Inglett | 195/66 |
| 3,711,462 | 1/1973 | Abdo | 260/209 |
| 3,740,318 | 6/1973 | Churchill et al. | 195/65 |
| 3,827,938 | 8/1974 | Aunstrup et al. | 195/62 |
| 4,007,115 | 2/1977 | Howe | 210/665 |
| 4,886,602 | 12/1989 | Kuehne et al. | 210/637 |

FOREIGN PATENT DOCUMENTS

| 0216270 | 4/1987 | European Pat. Off. . |
| 0220921 | 5/1987 | European Pat. Off. . |
| 0232169 | 8/1987 | European Pat. Off. . |
| 0246678 | 11/1987 | European Pat. Off. . |
| 0247647 | 12/1987 | European Pat. Off. . |
| 0325348 | 7/1989 | European Pat. Off. . |
| 1800508 | 5/1969 | Germany . |
| 1807185 | 6/1969 | Germany . |
| 1492302 | 2/1970 | Germany . |
| 1810823 | 10/1970 | Germany . |
| 2026092 | 12/1970 | Germany . |
| 2224777 | 1/1973 | Germany . |
| 2334463 | 1/1974 | Germany . |
| 2551742 | 5/1976 | Germany . |
| 3730868 | 3/1989 | Germany . |
| 3917645 | 12/1989 | Germany . |
| 3911099 | 10/1990 | Germany . |
| 3915277 | 11/1990 | Germany . |
| 3930284 | 3/1991 | Germany . |
| 8801293 | 2/1988 | WIPO . |
| 9013632 | 11/1990 | WIPO . |

OTHER PUBLICATIONS

Chemical Abstracts, vol. 107, No. 15, Oct. 12, 1987, Columbus, Ohio; Abstract No. 129968D, "Purification of an Enzyme Concentrate", p. 345; Col. L (See Abstract).

Chemical Abstracts, vol. 87, No. 1, Jul. 04, 1976, Columbus, Ohio; Abstract No. 4003x, I Alemzadeh et al.: "bacterial flocculation with sodium bentonite", p. 334; Col. R; (See Abstract).

*Primary Examiner*—Ivars Cintins
*Attorney, Agent, or Firm*—Wayne C. Jaeschke; Norvell E. Wisdom, Jr.; Frank S. Chow

[57] ABSTRACT

In a process for separating the exocellular proteins from the micro-organisms of a filtered fermentation liquor, the removal of solid is to be improved while retaining the useful substance. This is achieved by, in a first stage, removing substances preventing protein precipitation with the aid of a solid adsorption agent; concentrating the remaining solution to a protein content of about 30 to 40% by weight; and then precipitating and separating the protein, optionally with the addition of precipitants for protein to accelerate the precipitation, at pH values between 6 and 10.

21 Claims, No Drawings

PRECIPITATION PROCESS FOR EXOCELLULAR PROTEINS

FIELD OF THE INVENTION

This invention relates to a process for the purification and separation of exocellular proteins from fermenter broths. More particularly, the invention relates to a process for separating enzymes in solid form, coloring and odor-emitting substances being removed.

STATEMENT OF RELATED ART

Numerous enzymes, especially hydrolases, such as for example proteases, amylases or lipases, are produced by fermentation of microorganisms. Suitable microorganisms and processes for their production are described, for example, in the following patents and patent applications: DE 18 00 508, DE 22 24 777, DE 25 51 742, U.S. Pat. No. 3,827,938, WO 88/01293, DE 18 07 185, U.S. Pat. No. 3,740,318, DE 23 34 463, DE 20 26 092, EP 0 232 169, EP 0 220 921, EP 0 247 647 and EP 0 246 678.

Strongly coloring or strong-smelling impurities are unacceptable for numerous applications, for example for the use of the enzyme solutions in liquid detergents. Accordingly, in the industrial production of the enzymes, the impurities tend to be removed by precipitation processes. However, hitherto known precipitation processes have the disadvantage that considerable losses of yield have to be accepted in order to obtain good color quality. To counteract these difficulties, German patent application P 39 11 099.0 describes a precipitation process in which a masking agent is added to an enzyme solution produced by fermentation and a precipitate is subsequently prepared by adding two water-soluble, mutually precipitating ionic compounds in any order and optionally introducing other adsorbents, for example active carbon.

According to German patent application DE 38 21 151, fermenter broths and/or enzyme solutions are provided with reducing additives in order to reduce odor emission and to improve color quality.

A similar process is described in German patent application P 39 30 284.9, according to which cells of fungi, plants and/or bacteria or cell wall fragments of the above-mentioned organisms are added as selective adsorbents to a fermenter broth. German patent application P 39 15 277.4 also describes a similar process in which an acidic aqueous solution of an aluminum salt and, optionally, additional precipitants are added to the enzyme solution above a pH value between 5 and 11, water-soluble constituents are removed and a masking agent, such as an acid of boron or the like, is added after precipitation.

All the above-mentioned processes are based on the idea of binding the troublesome constituents to the surface of an adsorbent or co-precipitating them with the precipitate of an adsorbent produced in situ, so that an enzyme solution of improved purity remains behind. Although very pure enzyme solutions can be obtained by these processes, the enzyme yield naturally decreases with increasing purification, so that a compromise always has to be made between good quality and good quantity.

It is already known that proteins can be separated from fermenter solutions by precipitation of the proteins themselves rather than the troublesome impurities. However, where the usual precipitants are used in the usual concentrations, the impurities are co-precipitated so that the required purity cannot be obtained in this way.

DESCRIPTION OF THE INVENTION

SUMMARY OF THE INVENTION

The present invention is based on the surprising observation that the concentration precipitation of proteins, particularly hydrolases, is possible when certain substances evidently omnipresent in fermenter broths, which prevent concentration precipitation, are removed by a preliminary treatment with an adsorbent.

Accordingly, the present invention relates to a process for the separation of exocellular proteins of microorganisms from a filtered fermenter broth, characterized in that, in a first step, substances which impede precipitation of the proteins are removed by means of a solid adsorbent, the remaining solution is concentrated to a protein content of around 30 to 40% by weight and the protein is subsequently precipitated at pH values of 6 to 10 and removed, precipitants for proteins optionally being added to accelerate the precipitation process.

It is possible by the process according to the invention to purify numerous proteins which are produced by fermentation of microorganisms and which are present as exocellular proteins in the fermenter broths. For example, it may be used in particular for the production of enzymes, for example for the production of proteases, amylases, cellulases, xylanases, pentosanases or lipases. The process according to the invention is particularly suitable for the production of proteases, particularly alkaline proteases, such as serine proteases.

The fermenter solutions suitable for the process according to the invention preferably emanate from the cultivation of microorganisms, such as bacteria or fungi, more particularly from the cultivation of bacillus strains, for example strains of *Bacillus subtilis, Bacillus licheniformis, Bacillus lentus* or the like.

DESCRIPTION OF PREFERRED EMBODIMENTS

According to the invention, the fermenter broths are first treated with an adsorbent. To this end, the adsorbent is added in quantities of typically 0.5 to 10% by weight, based on protein solution. Suitable adsorbents are, for example, silicate-containing adsorbents, such as layer silicates, particularly bentonites. Of the bentonites, acid-activated bentonites are particularly suitable. Thus, an acid-activated bentonite having a montmorillonite index of 70 and a fineness of 93%<100 µ may be used as a particularly preferred bentonite.

Instead of or in addition to the bentonites, aluminum oxide hydrates or, quite generally, aluminum salts which form separable precipitates in the pH range around the neutral point of the protein solutions, may also be used as precipitants. Aluminum hydroxychlorides are preferably used as the aluminum salts. In the context of the invention, aluminum hydroxychlorides are understood to be chlorohydroxy compounds of aluminum, for example $(Al_2(OH)_5Cl)$ containing 2 to 3 moles of water of crystallization. Preferred materials are technical grades, for example of the type used for the purification of water. Other water-soluble aluminum salts, which form precipitates of aluminum hydroxides when the pH value is raised into the neutral range, are also suitable. The aluminum salts used in accordance with the invention are added to the enzyme solutions in the form of acidic aqueous solutions. These acidic solutions have a pH value of 3 to 4 and a concentration of 10 to 50% by weight. Solutions having a concentration of around 20% by weight have also proved to be favorable. In addition, aluminum hydroxychloride may also be directly stirred into the enzyme solutions in powder form. However, this is less preferred.

The enzyme solutions should have a pH value during the precipitation process in the range from 5 to 11 and preferably in the range from 5 to 8, because, beyond these pH limits, enzyme stability can be adversely affected and, in addition, the precipitant could be partly dissolved again. Accordingly, it is important to ensure that the pH value does not fall below 5 on addition of the precipitant. This may be prevented, for example, by addition of alkaline solutions, for example sodium hydroxide or potassium hydroxide. Buffer solutions may also be added, although they should be adapted to the precipitant.

The quantity of aluminum salt to be used is determined by the degree of purification to be achieved. For many technical applications, quantities of 1 to 5% by weight would appear to be preferable, although purification effects are even obtained with smaller quantities, for example beyond 0.5% by weight. Although larger quantities, for example up to 10% by weight, may be used, they are often not advisable on economic grounds.

In another embodiment of the invention, insoluble calcium salts may also be used for precipitation. It is preferred to produce calcium phosphates in situ in the protein solutions.

The ratio of the calcium salt to the ratio of the phosphorus acid salt is preferably selected so that the molar ratio of calcium to phosphorus is between 1.7 and 2.5:1. It has been found in this regard that calcium phosphates having a predominantly amorphous structure and a large surface are formed under these conditions, representing favorable adsorbents for the colored impurities to be precipitated. The quantity of precipitant, based on enzyme solution, is typically between 0.5 and 20% by weight.

Another adsorbent which may be used in addition to or instead of the adsorbents mentioned is active carbon.

In another embodiment of the invention, a masking agent may be added to the enzyme solutions before or after precipitation. It is preferred to add the masking agent before precipitation because less enzyme activity is lost in this way.

Acids of boron and sulfurous acids and alkali metal salts thereof may be added as masking agents. The quantities to be added are between 0.5 and 5% by weight and preferably between 1 and 3% by weight, based on enzyme solutions, larger quantities being inappropriate primarily on economic grounds. Suitable acids of boron are boric acid, metaboric acid and/or pentaboric acid. Accordingly, particularly suitable alkali metal salts are sodium borate, sodium metaborate, borax or sodium pentaborate. Sodium sulfite is also suitable.

Other suitable masking agents which may be used together with or instead of those mentioned above are dicarboxylic acids and/or hydroxycarboxylic acids containing 3 to 10 carbon atoms. Hydroxydicarboxylic acids, particularly citric acid, tartaric acid and isomers thereof are preferred. The quantity added is between 1 and 5% by weight. In this case, too, larger additions are inappropriate primarily for economic reasons and not because of any reduction in the technical effects obtained.

After the treatment with the adsorbent, the enzyme solution is concentrated. The protein content is preferably adjusted to between 40 and 50% by weight. The pH value of the preparation should be near the neutral point. The pH is preferably adjusted to a value of 7.5 to 9. This applies in particular to hydrolases and more especially to proteases.

Various processes are available to the expert for producing the concentrated enzyme solutions. Thus, micro filtration and/or ultrafiltration may be used and the enzyme solutions obtained may be brought to even higher concentrations either beforehand or afterwards by distilling off water under reduced pressure, for example in a thin film evaporator. In one particularly preferred process, the enzyme solutions are first prepurified by microfiltration and ultrafiltration, subsequently precipitated and finally concentrated by evaporation. In this process, the micro filtration and ultrafiltration steps are carried out in particular as described in German patent application DE 37 30 868. This patent application describes a process for the separation of biotechnologically produced useful materials from a fermenter broth by crossflow microfiltration and/or ultrafiltration using at least two modules arranged in tandem and equipped with porous membranes for each stage, characterized in that a different excess pressure relative to the ambient pressure is applied to each module on the permeate side. To carry out this process, a crossflow rate of more than 4 m/sec is preferably used in the microfiltration stage and inorganic materials, such as aluminum oxide, silicon carbide or zirconium dioxide on a support, are preferably used as the membrane materials.

The concentrated protein solutions prepared in the above-described stages of the process according to the invention are finally subjected to a precipitation step. To this end, the protein is allowed to precipitate in the absence of other substances by cooling the solution to near its freezing point and/or by leaving the solution standing. Thus, it is sufficient in many cases to cool the solution to +5° C. and simply to leave it standing overnight.

It is of course possible also to treat the concentrated protein solution by addition of protein precipitants and then to precipitate the proteins. However, this procedure is not particularly preferred. Suitable protein precipitants are, for example, soluble alkali metal salts, which may be used in quantities of 1 to 5% by weight, water-miscible organic solvents which may be used in quantities of 5 to 20% by weight or water-soluble polymers which may be used in quantities of 0.1 to 5% by weight. Preferred soluble alkali metal salts are sodium chloride, sodium sulfate, calcium chloride and the like. Suitable water-miscible solvents are monohydric and dihydric alcohols such as, for example, ethylene glycol, propylene glycol or even methanol, ethanol or acetone. Suitable water-soluble polymers are polyethylene glycol, polypropylene glycol or polyacrylamide.

The precipitated proteins obtained by the process according to the invention may be further processed in the usual way. Thus, aqueous or aqueous organic protein solutions, for example enzyme concentrate solutions, may be prepared from them. On the other hand, they may also be made up into solid products by drying the precipitated proteins or formulating them together with additives, for example to solid enzyme preparations.

EXAMPLES

Example 1

200 l of a fermenter broth having a specific protease activity of 34850 HPE/g were prepared by fermentation of a *Bacillus licheniformis* strain, which produces an exocellular protease of *Bacillus lentus*, and further processed as follows:

Microfiltration

Apparatus:

| | |
|---|---|
| Type | Tube modules Pilot plant 2S151, manufactured by TECHSEP, France |
| Filter area | 2 × 3.4 m² (2 modules in tandem) |
| Membrane material | Type M14, zirconium oxide on graphite |
| Cutoff limit | 0.14 µm |

Operating conditions:

| | | |
|---|---|---|
| Working temperature | 40° C. | |
| pH in the retentate | 8 | Adjusted with 30% NaOH |
| Retentate crossflow | 4.8 m/s | (= 75 m³/h circulation) |
| Retentate inflow | 1000 l/h | |
| Mean transmembranal pressure | 0.5 bar | Adjusted for each module by correction of the permeate pressure |

Addition of the precipitant:

An aluminum oxide chloride hydrate (LOCRON®) was added to the protease solution in quantities of 50 g/l. A pH of 8.0 was adjusted with sodium hydroxide.

Preliminary dilution:

The 200 l of culture solution were diluted with 140 l of salt solution (NaCl industrial salt, techn. 90%) to reduce the solids content and the viscosity.

| | |
|---|---|
| Salt concentration | 10 g/l |
| Dilution γ | 0.59 |

Diafiltration:

A total of 850 l of salt solution (NaCl) was added to the retentate while keeping the adjusted concentration factor γ at 0.59.

| | |
|---|---|
| Salt concentration | 10 g/l |
| Relative diafiltrate volume | 4.25 l/l |
| Permeate flow density | 29 l/m²h |

Concentration:

| | |
|---|---|
| Finally, the retentate was concentrated to | 170 l. |
| Concentration γ | 1.2 |

Result:

A total of 1020 l of enzyme-containing permeate was obtained after diafiltration and concentration.

Specific protease activity    4520 HPE/g

Ultrafiltration

Apparatus:

| | |
|---|---|
| Type | Millipore spiral module |
| Filter area | 5.6 m² |
| Membrane material | Polysulfone |
| Cutoff limit | 10,000 daltons |

Operating conditions:

| | |
|---|---|
| Working temperature | 25° C. |
| Retentate inflow | 2500 l/h |
| Mean transmembranal pressure | 1 bar |

Concentration:

Concentration is continued to about 30 l. This corresponds to a reduction in volume by a factor of 34, compared with the starting quantity for culture solution

| | |
|---|---|
| concentration γ | 6.6. |

The permeate flow density falls during concentration from 20 l/m²h to 5 l/m²h.

Result:

| | |
|---|---|
| 30 l of concentrate | |
| Specific protease activity | 112000 HPE/g |

Thermal concentration

Apparatus:

| | |
|---|---|
| Type | α-Laval CTIB-2 Centritherm thin layer evaporator |
| Heating area | 0.09 m² |
| Evaporator capacity | 50 kg/h (water) |

Operating conditions:

| | |
|---|---|
| Primary steam temperature | 80° C. |
| Secondary steam temperature | 35° C. |
| Secondary steam pressure | 0.01 bar |

The apparatus has a capacity of 12 kg/h (inflow).

Concentration:

Concentration was continued beyond the usual level. Based on the starting quantity, a reduction in volume by a factor of more than 40 was achieved.

| | |
|---|---|
| Concentration in the stage γ | 6 |

Result:

4.9 kg DSV concentrate with

| | |
|---|---|
| dry matter | 42.4% |
| protease activity | 755,000 CPE/g |

The opaque thin-layer evaporator concentrate was left standing overnight at 5° C. A white precipitate separable in a suction filter was formed and proved to be precipitated enzyme protein.

HPE units:

In the standardized HPE method, the protease is incubated with denatured casein for 15 minutes at 50° C./pH 8.5, excess substrate is precipitated by trichloroacetic acid and the extinction of the alkalized supernatant liquid is measured at 290 nm (soluble aromatic peptides). Under standard conditions, 0.5 extinction units correspond to 10 HPE. The HPE method is comparable with the Anson method.

Enzyme activity unit CPE:

The test principle is based on the proteolytic degradation of N,N-dimethyl casein in sodium sulfite solution at 50° C. and subsequent color reaction of the released amino groups with trinitrobenzene sulfonic acid. The color complex is photometrically quantified at 425 nm and evaluated against a protease standard.

The invention claimed is:

1. A process for the separation of exocellular hydrolases of microorganisms from a fermenter broth which comprises the steps of:
   a. filtering the broth,
   b. removing substances which impede the precipitation of proteins from the filtered broth by contacting said broth with a solid adsorbent, c. concentrating the remaining solution to a protein content of about 30 to 40% by weight;

d. precipitating the protein at pH values of 6 to 10; and e. recovering said protein containing said hydrolases.

2. A process as claimed in claim 1, wherein precipitants for proteins are added during precipitation to accelerate the precipitation process.

3. A process as claimed in claim 1 wherein said hydrolases is a member selected from the group consisting of proteases, amylases, cellulases, xylanases, lipases and mixtures thereof.

4. A process as claimed in claim 3 wherein said proteases is an alkaline serine protease.

5. A process as claimed in claim 1, wherein the adsorbents are selected from the group consisting of bentonites, calcium phosphate, active carbon and aluminum salts.

6. A process as claimed in claim 5, wherein the adsorbents are calcium phosphates produced in situ from soluble calcium salts and soluble phosphates or phosphorus acids.

7. A process as claimed in claim 5, wherein the precipitants are aluminum oxide hydrates produced in situ from aluminum sulfate hydrates or aluminum chloride hydrates.

8. A process as claimed in claim 1, wherein, after the treatment with the adsorbent, the protein content of the remaining solution is adjusted to 40 to 50% by weight.

9. A process as claimed in claim 8, wherein the pH value of the solution remaining after treatment with the adsorbent is adjusted to a value of 7.5 to 9.

10. A process as claimed in claim 1, wherein enzyme-stabilizing agents selected from the group consisting of borates and polybasic carboxylic acids are added to the enzyme solutions before or after precipitation.

11. A process as claimed in claim 1 wherein in step c., the remaining solution is treated by microfiltration, ultrafiltration or evaporation of the water.

12. A process as claimed in claim 1, wherein the fermenter broth is prepurified by microfiltration or ultrafiltration before addition of the adsorbent and, after addition of the adsorbent and its separation, the solution obtained is concentrated by evaporation under reduced pressure.

13. A process as claimed in claim 1 wherein soluble alkali metal salts are added as protein precipitants in step d. in quantities of 1 to 5% by weight based on the protein solution.

14. A process as claimed in claim 1 wherein organic solvents are added as protein precipitants in step d. in quantities of 5 to 20% by weight, based on the protein solution.

15. A process as claimed in claim 1 wherein water-soluble polymers are added as protein precipitants in step d. of the process in quantities of 0.1 to 5% by weight, based on the protein.

16. A process as claimed in claim 1 wherein said hydrolases comprises alkaline proteases.

17. A process as claimed in claim 16, wherein the fermenter broth is prepurified by microfiltration or ultrafiltration before addition of the adsorbent and, after addition of the adsorbent and its separation, the solution obtained is concentrated by evaporation under reduced pressure.

18. A process as claimed in claim 16, wherein soluble alkali metal salts are added as protein precipitants in the step d in quantities of 1 to 5% by weight, based on protein solution.

19. A process as claimed in claim 16, wherein organic solvents are added as protein precipitants in the step d of the process in quantities of 5 to 20% by weight, based on protein.

20. A process as claimed in claim 16, wherein water-soluble polypropylene glycols are added as protein precipitants in the step d of the process in quantities of 0.1 to 5% by weight, based on protein.

21. A process as claimed in claim 1 wherein said adsorbent is selected from the group consisting of (i) calcium phosphates produced in situ from soluble calcium salts and soluble phosphates or phosphorus acids and (ii) aluminum oxide hydrates produced in situ from aluminum sulfate hydrates or aluminum chloride hydrates.

* * * * *